(12) United States Patent
Ye et al.

(10) Patent No.: US 10,463,294 B2
(45) Date of Patent: Nov. 5, 2019

(54) VIDEO MONITORING TO DETECT SLEEP APNEA

(71) Applicant: Hill-Rom Services, Inc., Batesville, IN (US)

(72) Inventors: Chau Chong Ye, Singapore (SG); Yue Wang, Singapore (SG); Aye Aung, Singapore (SG)

(73) Assignee: Hill-Rom Services, Inc., Batesville, IN (US)

( * ) Notice: Subject to any disclaimer, the term of this patent is extended or adjusted under 35 U.S.C. 154(b) by 66 days.

(21) Appl. No.: 15/852,514

(22) Filed: Dec. 22, 2017

(65) Prior Publication Data

US 2018/0184970 A1    Jul. 5, 2018

Related U.S. Application Data

(60) Provisional application No. 62/440,160, filed on Dec. 29, 2016.

(51) Int. Cl.

| | |
|---|---|
| *A61B 5/113* | (2006.01) |
| *A61B 5/08* | (2006.01) |
| *A61B 5/00* | (2006.01) |
| *A61B 5/11* | (2006.01) |
| *A61B 5/024* | (2006.01) |
| *A61B 7/00* | (2006.01) |

(52) U.S. Cl.
CPC .......... *A61B 5/4818* (2013.01); *A61B 5/0803* (2013.01); *A61B 5/113* (2013.01); *A61B 5/4815* (2013.01); *A61B 5/02433* (2013.01); *A61B 5/1118* (2013.01); *A61B 5/4809* (2013.01); *A61B 5/4812* (2013.01); *A61B 7/003* (2013.01)

(58) Field of Classification Search
CPC ... G06T 7/0012; G06T 7/0014; G06T 7/0016; G06T 7/20; G06T 7/97; G06T 2207/10048; G06T 2207/30004; G06T 2207/30196; G06K 9/6202; G06K 2209/05; A61B 5/0816; A61B 5/0826; A61B 5/113; A61B 5/1135; A61B 5/4818
See application file for complete search history.

(56) References Cited

U.S. PATENT DOCUMENTS

| | | | |
|---|---|---|---|
| 6,062,216 A | 5/2000 | Corn | 128/204.23 |
| 7,035,432 B2 | 4/2006 | Szuba | 382/103 |
| 7,431,700 B2 | 10/2008 | Aoki et al. | 600/534 |
| 8,454,528 B2 | 6/2013 | Yuen et al. | 600/534 |
| 2006/0050930 A1* | 3/2006 | Szuba | A61B 5/4818 382/103 |

(Continued)

FOREIGN PATENT DOCUMENTS

| | | | |
|---|---|---|---|
| CA | 2 511 886 A1 | 1/2006 | H04N 7/18 |
| EP | 2 619 724 | 7/2013 | |

(Continued)

*Primary Examiner* — Andrew W Johns
(74) *Attorney, Agent, or Firm* — Merchant & Gould P.C.

(57) ABSTRACT

An example method for detecting a sleep apnea event can include: capturing a plurality of infrared images of an individual breathing; developing a spatial template based upon the infrared images, the spatial template defining at least a normal breathing pattern; using the spatial template to analyze further infrared images of the individual during sleep; and detecting a sleep apnea event using the spatial template and the further infrared images.

20 Claims, 5 Drawing Sheets

(56) References Cited

U.S. PATENT DOCUMENTS

| | | | |
|---|---|---|---|
| 2010/0041968 A1 | 2/2010 | Meschisen et al. | 600/301 |
| 2010/0063419 A1* | 3/2010 | Mostafavi et al. | A61B 5/1135 |
| | | | 600/587 |
| 2011/0144517 A1 | 6/2011 | Cervantes | 600/538 |
| 2014/0046184 A1 | 2/2014 | Heinrich et al. | A61B 5/4806 |
| 2014/0153794 A1 | 6/2014 | Varaklis et al. | G06T 7/0012 |
| 2014/0213845 A1 | 7/2014 | Bechtel et al. | A61M 5/1723 |
| 2014/0236036 A1 | 8/2014 | de Haan et al. | A61B 5/113 |
| 2014/0275832 A1 | 9/2014 | Muehlsteff et al. | |
| | | | A61B 5/6887 |
| 2014/0275833 A1 | 9/2014 | Vanderpohl, III | A61B 5/0077 |
| 2015/0141762 A1 | 5/2015 | Heinrich et al. | A61B 5/1116 |
| 2015/0148683 A1* | 5/2015 | Hermanne | A61B 5/1135 |
| | | | 600/475 |
| 2016/0210747 A1* | 7/2016 | Hay et al. | G06F 16/7335 |
| 2017/0169307 A1* | 6/2017 | Prasad et al. | A61B 5/0013 |

FOREIGN PATENT DOCUMENTS

| | | | | |
|---|---|---|---|---|
| EP | 2 930 637 A2 | 10/2015 | | G06F 19/00 |
| WO | WO-2012/040554 A2 * | 3/2012 | | G06Q 50/00 |
| WO | 2012123874 A1 | 9/2012 | | A61B 5/08 |
| WO | 2015059700 A1 | 4/2015 | | A61B 5/087 |

* cited by examiner

VIDEO MONITORING TO DETECT SLEEP APNEA

RELATED APPLICATION(S)

This patent application claims the benefit of U.S. Patent Application Ser. No. 62/440,160 filed on Dec. 29, 2016, the entirety of which is hereby incorporated by reference.

BACKGROUND

Many individuals suffer from the impacts of poor sleeping patterns. For example, obstructive sleep apnea affects around 4 percent of men and 2 percent of women. However, 80-90 percent of those individuals remain undiagnosed. Sleep apnea, if untreated, can have a significant impact on individuals who suffer from it. For instance, it can cause a reduction in cognitive function, cardiovascular disease, stroke, fatigue, and excessive daytime sleepiness. Current techniques to detect and diagnose such disorders can be costly, intrusive, and inaccurate.

SUMMARY

Embodiments of the disclosure are directed to a method for detecting a sleep apnea event, the method comprising: capturing a plurality of infrared images of an individual breathing; developing a spatial template based upon the infrared images, the spatial template defining at least a normal breathing pattern; using the spatial template to analyze further infrared images of the individual during sleep; and detecting a sleep apnea event using the spatial template and the further infrared images.

In another aspect, an example method for detecting a sleep apnea event can include: capturing a plurality of infrared images of an individual breathing; developing a spatial template based upon the infrared images, the spatial template defining at least a normal breathing pattern; determining a category of movement; using the spatial template and the category of movement to analyze further infrared images of the individual during sleep; and detecting a sleep apnea event using the spatial template and the further infrared images.

In yet another aspect, an example system for detecting a sleep apnea event can include: at least one camera for capturing a plurality of infrared images of an individual breathing; memory; and a processor programmed to execute one or more instructions stored on the memory to: develop a spatial template based upon the infrared images, the spatial template defining at least a normal breathing pattern; use the spatial template to analyze further infrared images of the individual during sleep; and detect a sleep apnea event using the spatial template and the further infrared images.

The details of one or more techniques are set forth in the accompanying drawings and the description below. Other features, objects, and advantages of these techniques will be apparent from the description, drawings, and claims.

DETAILED DESCRIPTION

The present disclosure is directed to systems and methods for detecting sleep apnea.

In one example, a system includes one or more infrared cameras that capture the video of a patient. This video is then processed to detect abnormal breathing events like sleep apnea.

More specifically, an image processing algorithm can be employed. This algorithm is created based upon machine learning techniques that are used to analyze the normal breathing pattern of the patient, which serves as reference for the detection of abnormal breathing, such as sleep apnea.

In some examples, this non-intrusive sleep apnea detection solution can be integrated with other systems, such as alerting systems and/or assistive systems to provide monitoring and resolution of sleep apnea events. For example, once the system detects an abnormal sleeping event like apnea, the system can be programmed to send one or more alerts to a caregiver. Similarly, the system can be programmed to activate a mechanism that physically assists the patient to address the apnea event, such as by opening his/her airway.

Figure 1:
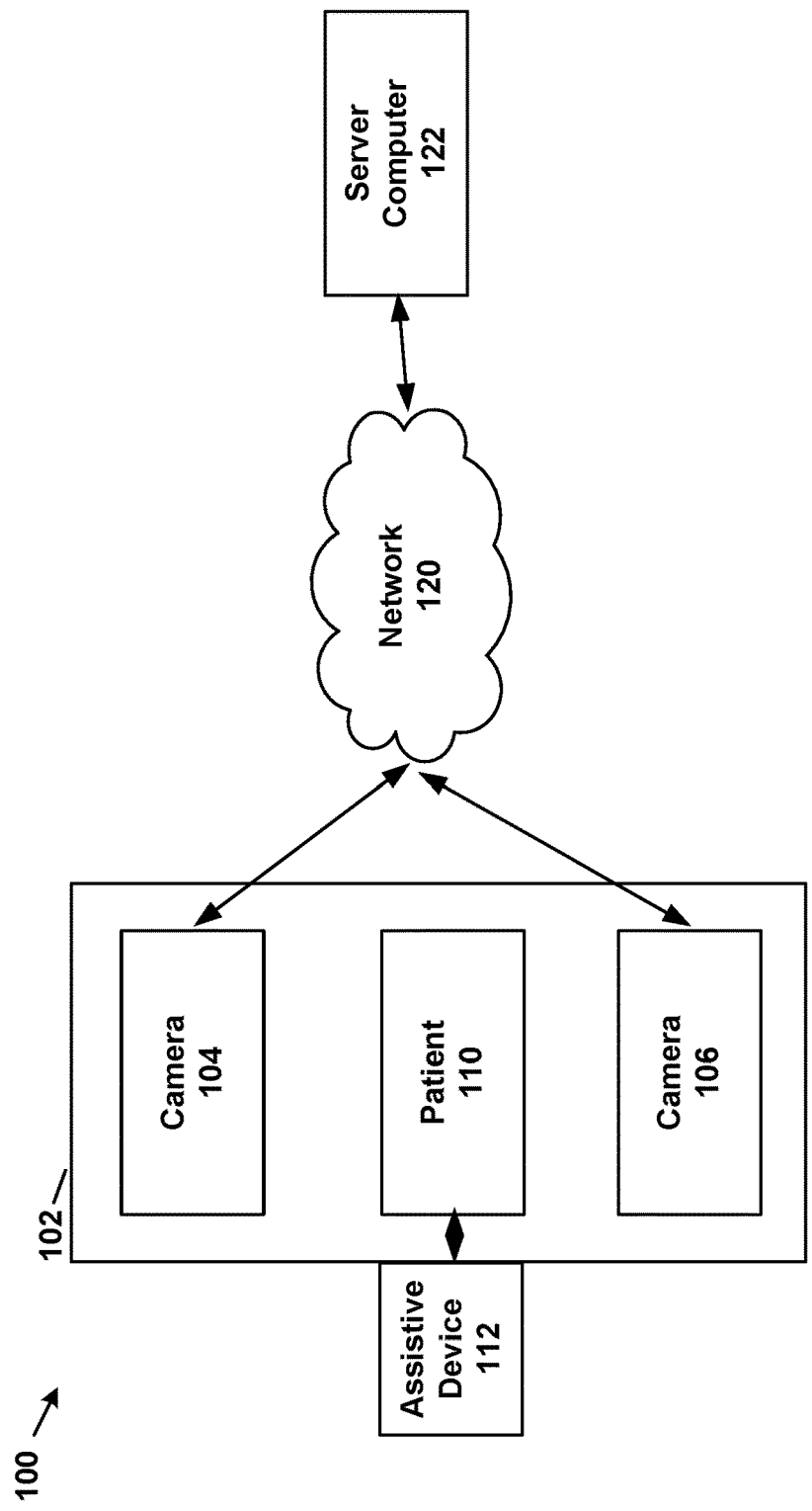
FIG. 1 shows an example environment including a patient, a plurality of cameras, and a computing device programmed to detect sleep apnea.

FIG. 1 shows an example environment 100, such as a hospital or clinical setting. In other examples, the environment 100 can be a bedroom or a sleeping area provided to a patient 110.

In this context, a patient support device 102, such as a mattress, provides support for the patient 110. One example of such a patient support device 104 is the TotalCare® P500 Intensive Care Bed manufactured by Hill-Rom of Batesville, Ind. Other configurations are possible.

One or more cameras are positioned within the environment 100. In this example, cameras 104, 106 are coupled to the support device 102, although other configurations are possible. For example, the cameras 104, 106 can be stand-alone devices or be coupled to other structures within the environment 100, such as a wall.

In these examples, the cameras 104, 106 are infrared cameras configured to capture infrared images of the patient 110 on the support device 102. Each of the cameras 104, 106 includes an infrared laser and a detector, such as a CMOS sensor, that captures three-dimensional imagery. The images that are captured by each of the cameras 104, 106 can be processed locally or remotely, as described further below, to detect abnormal sleeping patterns of the patient 110.

For example, as depicted, the cameras 104, 106 are programmed to transmit the captured infrared imagery to a server computer 122 through a network 120. The server computer 122 can be a central server that is programmed to process the imagery and/or allow a caregiver to monitor the patient 110. Further, various alerting can be provided to the caregiver, such as if the sleeping patterns fall outside a given norm, as describe below. In another example, the server computer 122 can be an electronic medical record (EMR) repository, and the imagery and/or data associated therewith can be captured within the EMR for the patient 110. Other configurations are possible.

In one example, the server computer 122 is programmed to analyze the imagery from the cameras 104, 106 and to automate the detection of abnormal sleep patterns, such as sleep apnea. In this example, the server computer 122 is programmed use machine learning to characterize normal breathing motion patterns, and use this to classify motion events such as normal breathing episodes, deep breathing episodes, apnea episodes and body movements. Such patterns can be associated with different signal level as well as spatiotemporal patterns.

The server computer 122 is also programmed to detect other episodic motion events associated with normal breathing that are more protracted during the sleeping period and has cyclic pattern. In addition, the server computer 122 is programmed to reject movement that is unassociated with breathing, such as the motion coming from other places (shoulder, throat, mouth, etc.). Such motion is more sporadic and has distinguishable spatial feature compared with that of breathing movements. In order to fit for the various use cases, the algorithm generated by the server computer 122 is configured to learn and generate a breathing motion spatial template and adapt to different body posture for the patient 110 (e.g., supine, left turn, right turn, prone).

Although the server computer 122 is depicted in a location remote from the patient 110 and the support device 102, in other embodiments the infrared video can be captured and processed by a computing device located at the support device 102.

Finally, the environment 100 can also optionally include an assistive device 112 that is associated with the patient 110. The assistive device 112 can be configured to passively and/or actively intervene during a negative event, such as a sleep apnea event. Examples of such devices include continuous positive airway pressure (CPAP) machines and implanted stimulation devices. Other configurations are possible.

Figure 2:
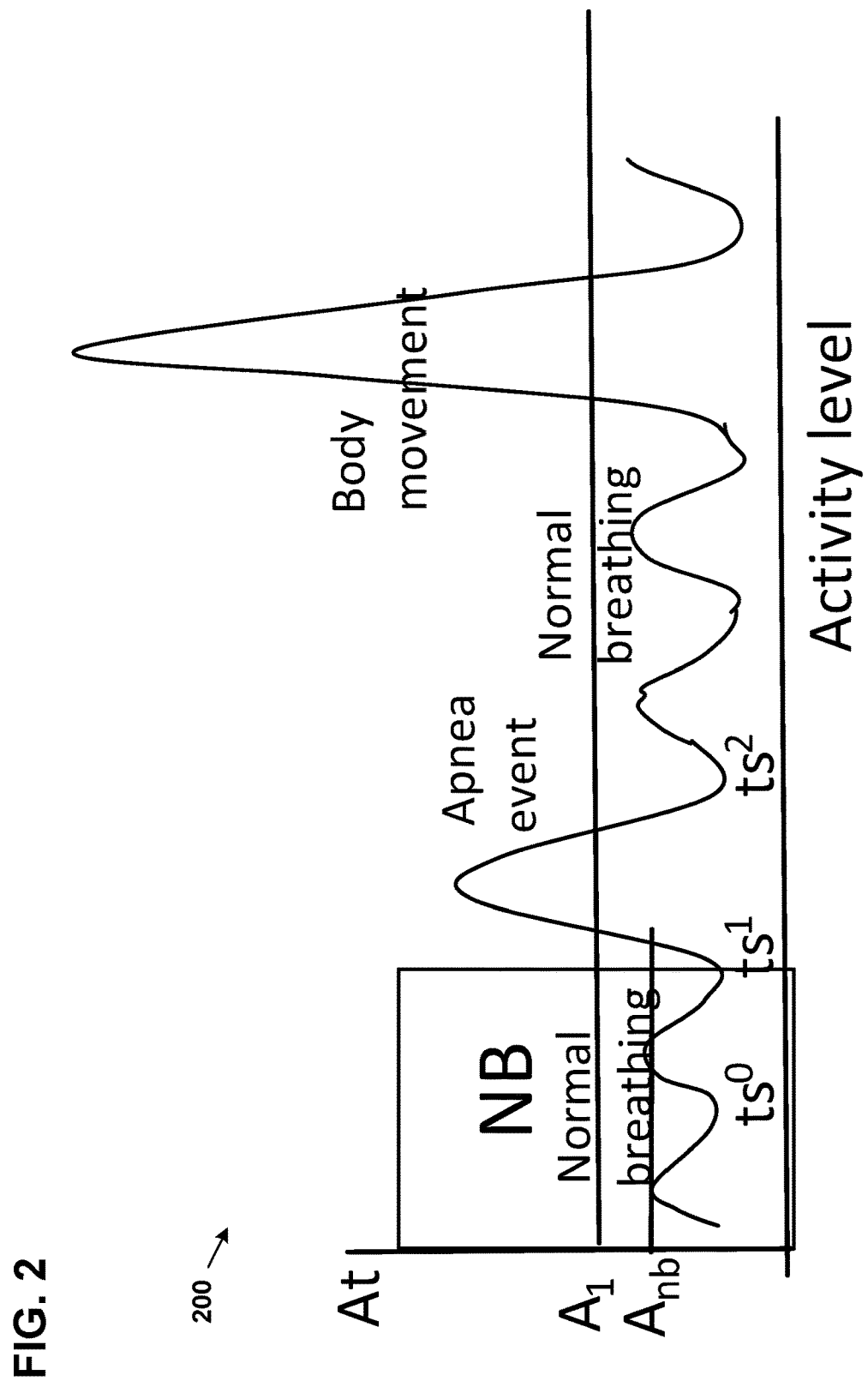
FIG. 2 shows an example spatial template that illustrates different breathing events for the patient of FIG. 1.

Referring now to FIG. 2, an example spatial template 200 is shown that illustrates different breathing events for the patient. This spatial template 200 is generated over time based upon the processing of the infrared imagery from the cameras 104, 106, as described further below.

As illustrated, the spatial template 200 illustrates a variety of categories of movement, like normal breathing (NB), as illustrated between times ts0 and ts1. An apnea event is illustrated at the interval between ts1 and ts2. Finally, normal breathing and body movement are shown after time ts2.

Over time, the server computer 122 is programmed to generate the spatial template 200 that allows the server computer 122 to distinguish between events like normal breathing, body movement, and apnea.

Figure 3:
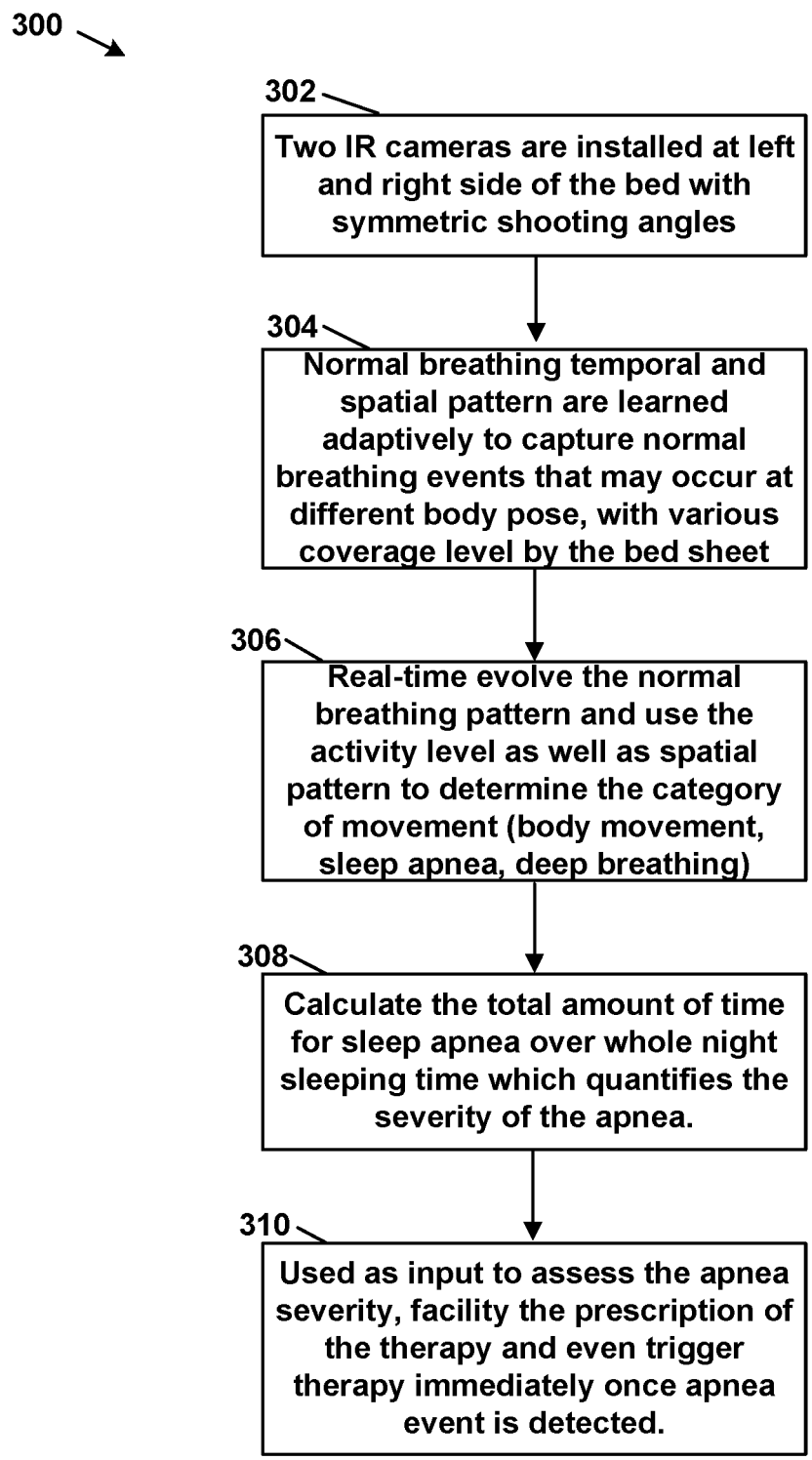
FIG. 3 shows an example method for detecting breathing events during sleep in the environment of FIG. 1.

Referring now to FIG. 3, an example method 300 for detecting breathing events during sleep is shown.

At operation 302, two or more infrared cameras are positioned as shown in FIG. 1. In this example, the cameras are positioned at strategic locations, such as right and left sides of the support device so that the infrared images captured by the cameras are symmetrically aligned.

Next, at operation 304, imagery is captured by the cameras of normal breathing patterns. This is done at a variety of body positions and with a variety of environmental factors, such as the position of a bed sheet being varied over time. This information is used to develop a spatial template.

At operation 306, the patient is monitored in near real-time during sleep. The activity level of the patient is used along with the spatial template that has been learned over time to categorize the breath movements for the patient during sleep. Different categories can include body movement, normal breathing, deep breathing, and sleep apnea.

Next, at operation 308, various trends are detected over time as the patient's sleeping patterns are assessed. For example, the total amount of time associated with apnea events can be calculated. This can be used to determine a severity of the apnea.

Finally, at operation 310, the data collected and developed can be used to assess the severity of the sleep apnea, as well as remedies associated with apnea. For example, should the events reach a threshold level, an alert can be triggered that is delivered to the patient and/or a caregiver. This will allow the caregiver to assess the issue and possibly prescribe remedial therapy.

In another example, the triggering of therapy at operation 310 can be accomplished using, for example, a mechanism that can physically alter a patient's breathing during an apnea event. For example, the detection of an apnea event can be used to trigger an implanted (e.g., stimulation device) or other device like a CPAP machine to provide assisted breathing and/or to otherwise clear the airway. Other configurations are possible.

Figure 4:
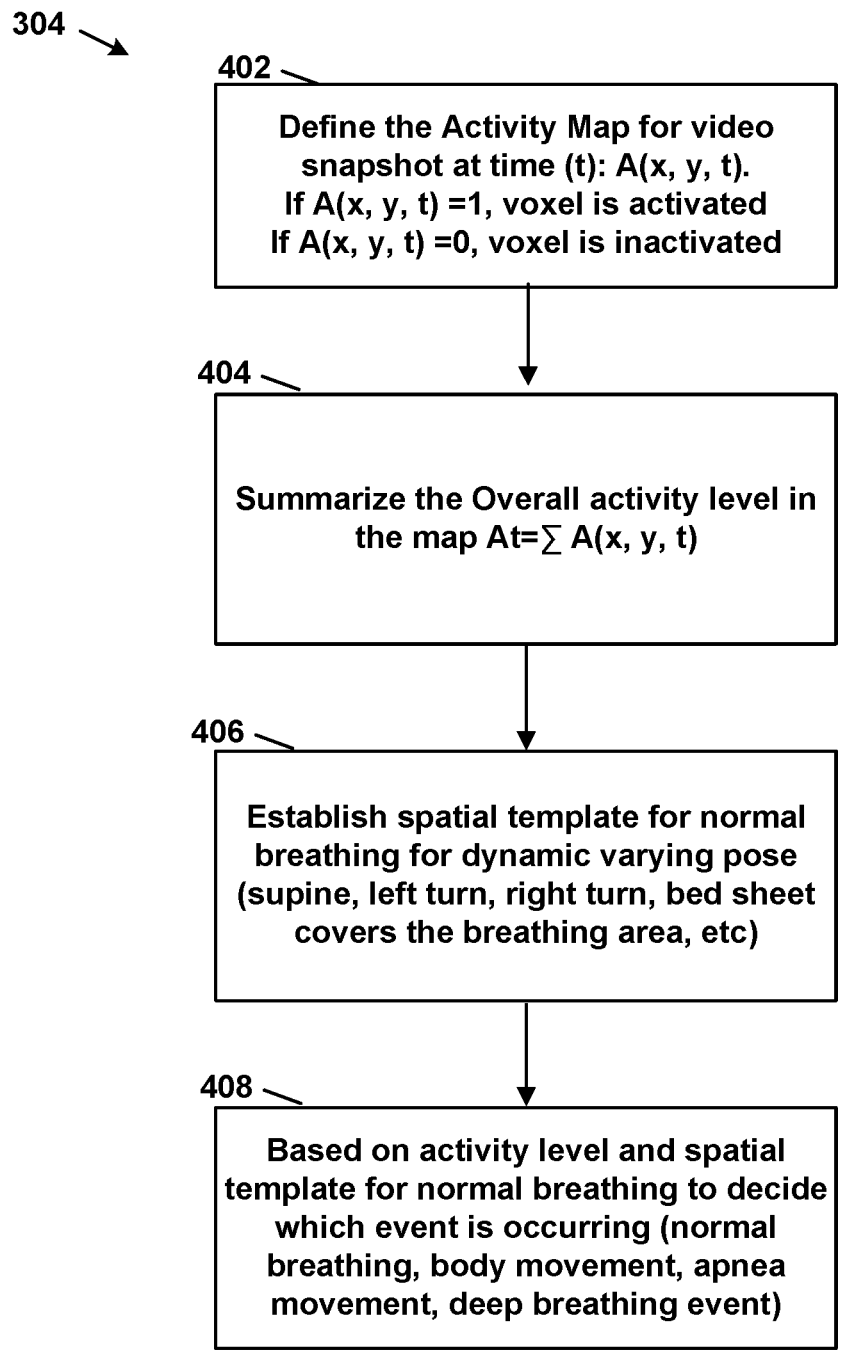
FIG. 4 shows additional details of the method for detecting breathing events during sleep of FIG. 3.

Referring now to FIG. 4, additional details are shown about the operation 306 for using the activity levels of the patient along with the learned spatial template to categorize the movement for the patient.

At operation 402, an activity map is generated for a plurality of the images from the video feed from the cameras. The activity map is generated at a time (t) and over the X and Y coordinates for each image. If the calculated activity value for a given area $A(x, y, t)$ is positive, then a voxel (i.e., an array of elements of volume that constitute a notional three-dimensional space) is activated for that image.

Next, at operation 404, the overall activity level is summed over multiple images. The spatial template for the various categories of movement and varying poses/environmental factors are then calculated in operation 406.

Finally, at operation 408, a sensed activity level and spatial template are used to determine what event is currently occurring for the patient. This can include a determination of the category of movement, like normal breathing or apnea.

In some embodiments, the spatial template for determining normal breathing is calculated as follows. First, at least two cycles are detected, which may be associated with the cyclical nature of normal breathing. At that point, the template (T) for normal breathing from is established from ts0 as follows:

Initialize $T(x, y, ts0)=0$
Update $T(x, y, t)$
Define the quality level $Q(t)=\Sigma T(x, y, t)$
$T_I(x, y, t)=\Delta$, IF $A(x, y, t)=1$, $T_I(x, y, t-1)>0$
$T_I(x, y, t)=\Delta/2$, IF $A(x, y, t)=1$, $T_I(x, y, t-1)=0$
$T_I(x, y, t)=T_I(x, y, t-1)-0.001\Delta$, IF $A(x, y, t)=0$, $T_I(x, y, t-1)>0$, $Q(t)>\kappa$ (where $\kappa$ determines if there is sufficient information needed for motion event classification)
$T_I(x, y, t)=0$, other cases The intermediate variable $T_I(x, y, t)$ is used to determine $T(x, y, t)$ as a binary template $T(x, y, t)=1$, IF $TI(x, y, t)>\Delta/2$ and $Q(t)>\kappa$; otherwise, $T(x, y, t)=0$.

If $At > A_1$ ($A_1=1.2A_{nb}$, $A_{nb}$ being the average of the maximal normal breathing activity), the evolution of the normal breathing template stops. After 5 more steps, the spatial template is used with matching logic to decide which event is occurring (normal breathing, body movement, apnea movement, deep breathing event).

When the At drops to another valley (such as at ts2 in FIG. 2), the server computer 122 is programmed to wait for a given number of cycles (e.g., two) to be observed at the similar activity level (e.g., as at ts1). Thereupon, the server computer 122 resumes the normal breathing spatial pattern extraction.

The template matching logic can be based on machine learning, where the Activity Map A(x, y, t) is used as feature, and a classification algorithm, such as a support vector machine (SVM), is used to classify into different event. Or, the classification can be accomplished by counting the ratio between voxels outside of the spatial template that overlap with A(x, y, t) and voxels within the spatial template that overlap with A(x, y, t). An empirically driven threshold can then be used to decide the movement category. In general, body movement has a highest ratio, followed by apnea movement and then by deep breathing.

Figure 5:
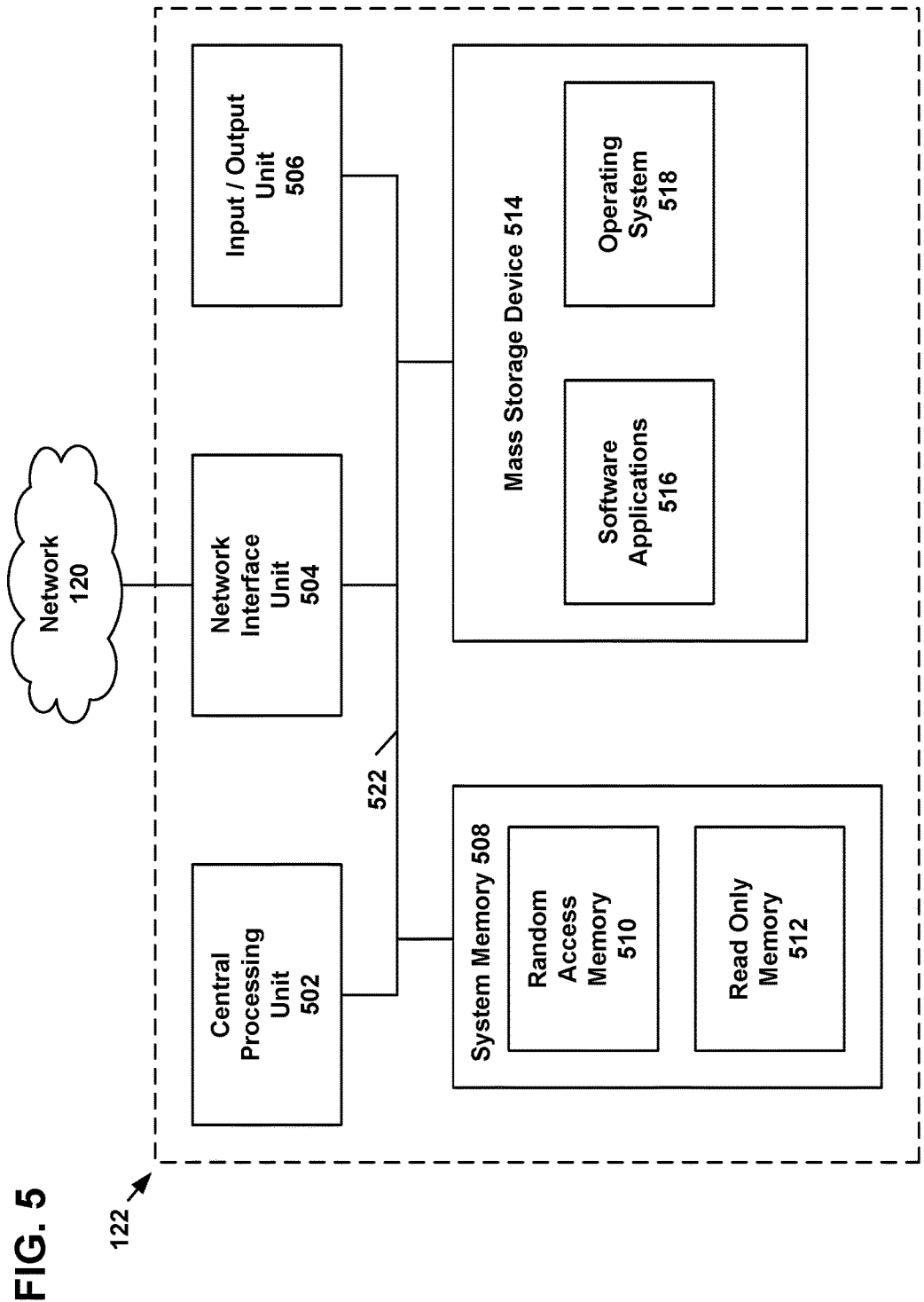
FIG. 5 shows example physical components of the server computer of FIG. 1.

There are various advantageous to the use of the spatial template as described herein. For example, extraction of the spatial template enables adaption to various breathing behaviors (e.g., shallow versus heavy breathing, mouth breathing, chest breathing, and abdominal breathing), so long as the breathing behavior has cyclic pattern. Further, the adaptive temporal activity tracking and spatial template learning enables robust evaluation of a range of scenarios with various body poses, body movements (i.e., head movement, limb movement, body rotation, and slight torso movement), As illustrated in FIG. 5, the server computer 122 includes at least one central processing unit ("CPU") 502, a system memory 508, and a system bus 522 that couples the system memory 508 to the CPU 502. The system memory 508 includes a random access memory ("RAM") 510 and a read-only memory ("ROM") 512. A basic input/output system contains the basic routines that help to transfer information between elements within the server computer 122, such as during startup, is stored in the ROM 512. The server computer 122 further includes a mass storage device 514. The mass storage device 514 is able to store software instructions and data.

The mass storage device 514 is connected to the CPU 502 through a mass storage controller (not shown) connected to the system bus 522. The mass storage device 514 and its associated computer-readable data storage media provide non-volatile, non-transitory storage for the server computer 122. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the server computer 122.

According to various embodiments, the server computer 122 may operate in a networked environment using logical connections to remote network devices through the network 120, such as a wireless network, the Internet, or another type of network. The server computer 122 may connect to the network 120 through a network interface unit 504 connected to the system bus 522. It should be appreciated that the network interface unit 504 may also be utilized to connect to other types of networks and remote computing systems. The server computer 122 also includes an input/output controller 506 for receiving and processing input from a number of other devices, including a touch user interface display screen, or another type of input device. Similarly, the input/output controller 506 may provide output to a touch user interface display screen or other type of output device.

As mentioned briefly above, the mass storage device 514 and the RAM 510 of the server computer 122 can store software instructions and data. The software instructions include an operating system 518 suitable for controlling the operation of the server computer 122. The mass storage device 514 and/or the RAM 510 also store software instructions, that when executed by the CPU 502, cause the server computer 122 to provide the functionality of the server computer 122 discussed in this document. For example, the mass storage device 514 and/or the RAM 510 can store software instructions that, when executed by the CPU 502, cause the server computer 122 to learn and detect sleeping events and patterns as describe herein.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A method for detecting a sleep apnea event, the method comprising:
    capturing a plurality of infrared images of an individual breathing;
    developing a spatial template based upon the infrared images, the spatial template defining at least a normal breathing pattern;
    using the spatial template to analyze further infrared images of the individual during sleep; and
    detecting a sleep apnea event using the spatial template and the further infrared images.

2. The method of claim 1, further comprising using a plurality of infrared cameras to capture the plurality of infrared images.

3. The method of claim 2, further comprising positioning a first infrared camera at a right side of the individual and a second infrared camera at a left side of the individual.

4. The method of claim 2, further comprising positioning the plurality of infrared cameras at symmetric shooting angles.

5. The method of claim 1, further comprising developing the spatial template with the individual positioned at different body positions.

6. The method of claim 1, further comprising calculating a total time for sleep apnea over a specific period based upon one or more detected sleep apnea events.

7. The method of claim 1, further comprising determining a category of movement.

8. The method of claim 7, further comprising using an activity level to determine the category of movement.

9. The method of claim 8, further comprising selecting among body movement, sleep apnea, and deep breathing as the category of movement.

10. The method of claim 1, further comprising triggering therapy when the sleep apnea event is detected.

11. A method for detecting a sleep apnea event, the method comprising:
- capturing a plurality of infrared images of an individual breathing;
- developing a spatial template based upon the infrared images, the spatial template defining at least a normal breathing pattern;
- determining a category of movement;
- using the spatial template and the category of movement to analyze further infrared images of the individual during sleep; and
- detecting a sleep apnea event using the spatial template and the further infrared images.

12. The method of claim 11, further comprising using a plurality of infrared cameras to capture the plurality of infrared images.

13. The method of claim 11, further comprising developing the spatial template with the individual positioned at different body positions.

14. The method of claim 11, further comprising using an activity level to determine the category of movement.

15. The method of claim 11, further comprising selecting among body movement, sleep apnea, and deep breathing as the category of movement.

16. A system for detecting a sleep apnea event, the system comprising:
- at least one camera for capturing a plurality of infrared images of an individual breathing;
- memory; and
- a processor programmed to execute one or more instructions stored on the memory to:
  - develop a spatial template based upon the infrared images, the spatial template defining at least a normal breathing pattern;
  - use the spatial template to analyze further infrared images of the individual during sleep; and
  - detect a sleep apnea event using the spatial template and the further infrared images.

17. The system of claim 16, further comprising a plurality of infrared cameras to capture the plurality of infrared images.

18. The system of claim 17, further comprising a first infrared camera positioned at a right side of the individual and a second infrared camera positioned at a left side of the individual.

19. The system of claim 17, wherein the plurality of infrared cameras are positioned at symmetric shooting angles.

20. The system of claim 17, wherein the processor executes further instructions to develop the spatial template with the individual positioned at different body positions.

* * * * *